United States Patent [19]

Leijd

[11] Patent Number: 5,718,675
[45] Date of Patent: Feb. 17, 1998

[54] SAFETY TAMPON

[75] Inventor: Nicklas Leijd, Haninge, Sweden

[73] Assignee: Bo Andersson, Madrid, Spain

[21] Appl. No.: 628,695

[22] PCT Filed: Nov. 5, 1993

[86] PCT No.: PCT/SE93/00922

§ 371 Date: Apr. 17, 1996

§ 102(e) Date: Apr. 17, 1996

[87] PCT Pub. No.: WO95/13040

PCT Pub. Date: May 18, 1995

[51] Int. Cl.$^6$ .................................................. A61M 31/00
[52] U.S. Cl. ........................... 604/11; 604/330; 604/904
[58] Field of Search ............................ 604/904, 11–18, 604/380

[56] References Cited

U.S. PATENT DOCUMENTS

| | | |
|---|---|---|
| 839,061 | 12/1906 | Farjas .............................. 604/11 |
| 2,355,628 | 8/1944 | Calhoun ........................ 604/904 |
| 3,712,305 | 1/1973 | Wennerblom et al. . |
| 3,845,766 | 11/1974 | Zöller . |
| 4,027,673 | 6/1977 | Poncy et al. .................. 604/904 |
| 4,108,180 | 8/1978 | Moehrle . |
| 4,335,720 | 6/1982 | Glassman ....................... 604/904 |
| 4,374,522 | 2/1983 | Olevsky ........................ 604/904 |
| 5,263,926 | 11/1993 | Wilk ............................... 604/11 |

Primary Examiner—David Isabella
Assistant Examiner—David J. Cho
Attorney, Agent, or Firm—Nixon & Vanderhye P.C.

[57] ABSTRACT

A reusable tampon includes an interior cavity which can be filled with absorbent material. The absorbent material can be removed and new absorbent material inserted in its place through an opening in an upper portion of the tampon. The tampon has a body which is hollow and formed of flexible, human tissue-friendly material. The lower part of the body is closed and has a semi-circular shape. Inflow apertures in the body of the tampon are inclined inwardly and toward the semi-circular lower portion of the body, allowing menstrual blood to pass into the interior cavity. Axially extending inflow grooves may also be provided. The tampon may have an elliptical cross-section, and a plurality of small balls of highly aborbent material may be disposed in the interior cavity.

14 Claims, 1 Drawing Sheet

FIG. 1          FIG. 2          FIG. 3
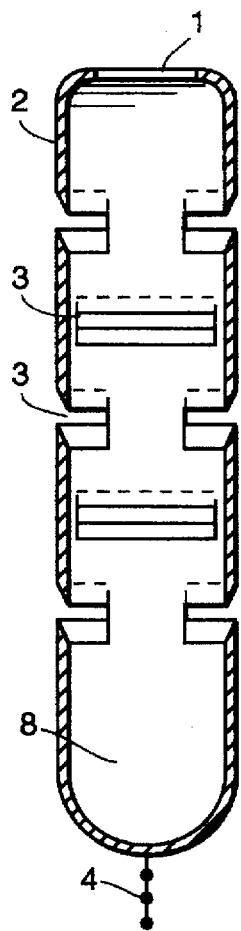 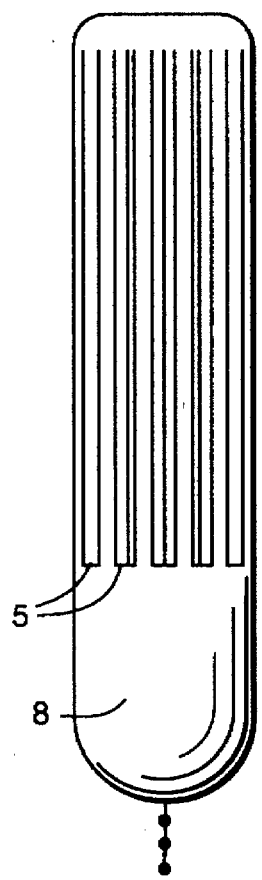 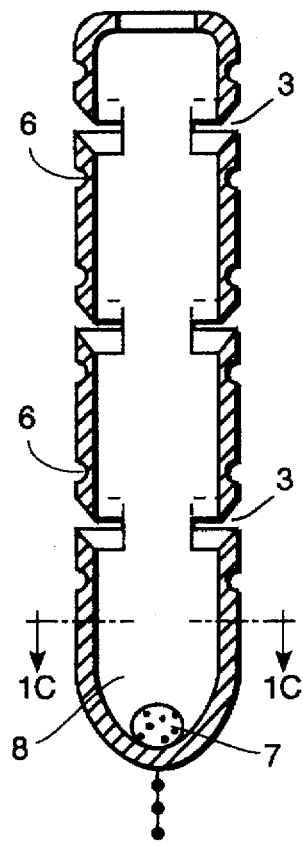
FIG. 1A          FIG. 1B          FIG. 1C
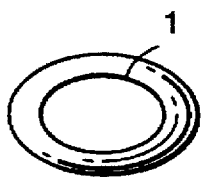 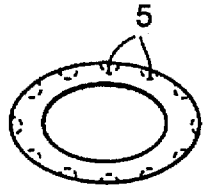 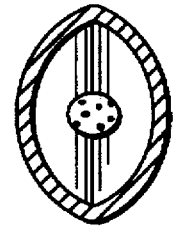

SAFETY TAMPON

CROSS-REFERENCE TO RELATED APPLICATION

This application is the U.S. National phase of PCT/SE93/00922 filed Nov. 5, 1993.

BACKGROUND AND SUMMARY OF THE INVENTION

The present invention relates to a hollow tampon manufactured from hygienic and tissue-friendly flexible material, with which the user herself fills the tampon with absorbent material which is then discarded after use, whereafter the tampon is refilled with absorbent material by the user for further use. In other words, the safety tampon is reusable.

The amount of menstrual fluid discharged from women will very from person to person. The safety tampon provides women with the possibility of modifying their own need for absorbent material during their menstruation periods.

As a result of its design, the design of the safety tampon eliminates saturation and also the dripping effect of tampons—soiling of clothes and possibly also furniture. The inventive tampon is therefore called a safety tampon, since it affords a degree of safety or security to the wearer.

It is generally known that tampons commercially available at present are liable to injure the extremely sensitive and easily irritated walls of the vagina of the female wearer to a greater or lesser extent. Furthermore, the microscopic injuries caused to the mucous membrane and to the walls of the vagina of women who use tampons render these parts of the body extremely receptive to infectious diseases of diverse kinds.

These dangers and related dangers and discomfort are eliminated by the present invention as a result of the following properties.

1) The tampon is counteractive to tampon saturation and droplet effect.

2) The design of the safety tampon and the tissue-friendly material from which it is made eliminates the hazard of injury to the vagina of the female wearer.

The invention thus relates to a hollow tampon which is made of flexible, tissue-friendly material and which includes on the outside of the tampon a plurality of downwardly inclined so-called inflow apertures through which menstrual fluid is able to pass to a closed space located in the lowermost part of the tampon. The user has earlier placed in this space, or cavity, an absorbent material—a highly absorbent material—as necessary. In other words, the user herself fills and refills the tampon with absorbent material and discards this material after use, and then refills the same tampon with absorbent material to obtain an effective tampon. This procedure enables the safety tampon to be reused over a long period of time.

BRIEF DESCRIPTION OF THE DRAWINGS

The invention will now be described in more detail with reference to an exemplifying embodiment thereof and also with reference to the accompanying drawing, in which FIG. 1 is a schematic longitudinal section view of one exemplifying embodiment of an inventive tampon;

FIG. 2 illustrates schematically solely the axially extending flow grooves which facilitate the flow of menstrual fluid to the so-called inflow apertures, from which the fluid then passes to the closed space in the lowermost part of the tampon; and FIG. 3 is a longitudinal, schematic section view of "radial pits or recesses" whose function is to facilitate placement of the tampon in a fixed position in the vagina. This longitudinal section view also shows the downwardly inclined, so-called inflow apertures, and also a ball of highly absorbent material in the closed space in the lowermost part of the tampon.

DETAILED DESCRIPTION OF THE DRAWINGS

The tampon can be said to have an elliptical shape formed by tissue-friendly, flexible material over whose upper part there has been inserted an oval profile and an elliptical opening. The lower part of the tampon is closed in a semi-circular shape.

FIG. 1. The reference numeral 1 identifies an opening in the upper part of the tampon which allows menstrual blood to pass to the closed space in the lowermost part of the tampon. The opening is also used by the wearer to remove used absorbent material and also to insert new unused absorbent material.

The reference numeral 2 identifies the outside of the tampon.

The reference numeral 3 identifies the plurality of so-called downwardly-inclined inflow apertures on the outside of the tampon. In order to obtain a maximum receptive effect, the so-called downwardly-inclined inflow apertures 3 have been placed as shown in FIG. 1 (a schematic longitudinal section view).

The reference 4 identifies an appendage connected to the lower, closed semi-circular part of the tampon. The appendage is used to facilitate removal of the tampon from the vagina of the female wearer.

FIG. 2. The reference numeral 5 identifies the axially extending, so-called inflow grooves which facilitate flow of menstrual blood to the so-called downwardly-inclined inflow apertures 3, from where the blood passes to the closed space in the lowermost part of the tampon. The so-called inflow grooves 5 depart from the upper part of the tampon and extend to the so-called downwardly-inclined inflow apertures 3 located lowermost in the tampon.

FIG. 3. The reference numeral 6 identifies "radial pits or recesses" provided on the outside of the tampon, these pits functioning to facilitate fixed positioning of the tampon in the vagina.

The reference numeral 3 identifies the plurality of so-called downwardly-inclined inflow apertures on the outside of the tampon which, when the tampon is inserted in position in the vagina of the wearer, permits menstrual blood to pass to the lower part of the tampon and therewith to its closed space. In order to obtain a maximum receptive effect, the so-called downwardly-inclined inflow apertures are placed in the positions shown in the schematic longitudinal section view of FIGS. 1 and 3.

The reference numeral 4 identifies a ball of highly absorbent material which is located in the closed space in the lower part of the tampon.

When the user so desires, she replaces the consumed, wet material with new, unused absorbent material in the closed space of the tampon, precisely as she herself desires.

The reference numeral 8 identifies the so-called depositing space.

It is thought that the manner in which the inventive safety tampon works will be understood in all essentials from the aforegoing. As a result of its design, the safety tampon eliminates the saturation and dripping effect of tampons— soiling of clothes and possibly also furniture. The invention enables women to adapt conveniently the consumption of "absorbent material" during a menstruation period, in accordance with her own requirements. The safety tampon can be reused over a long period of time, which means that the safety tampon is economically rewarding to the user.

I claim:

1. A tampon comprising:
   a hollow substantially cylindrical body of flexible, human tissue-friendly material, having a lower portion, and having an upper portion including an opening;
   said lower portion of said tampon body being closed and semi-circular in shape;
   said hollow body and closed lower portion defining an interior cavity for the receipt and storage of menstrual blood;
   a plurality of inflow apertures formed in said body and inclined toward said closed lower portion, said apertures providing for the flow of menstrual blood therethrough to said interior cavity;
   said interior cavity being accessible from the exterior of said body so that said cavity may be filled with absorbent material, and the absorbent material may be removed therefrom;
   said upper portion being disposed opposite said closed lower portion, and said opening providing for the insertion of absorbent material into said interior cavity, and removal of used absorbent material from said interior cavity; and
   wherein said body further comprises inflow grooves extending from said upper portion of said tampon body axially along the exterior thereof and terminating at said inclined inflow apertures.

2. A tampon as recited in claim 1 further comprising a plurality of balls of highly absorbent material disposed within said interior cavity.

3. A tampon as recited in claim 2 wherein said body has a substantially elliptical configuration in cross-section.

4. A tampon as recited in claim 1 wherein said body has a substantially elliptical configuration in cross-section.

5. A tampon comprising:
   a substantially cylindrical hollow body of flexible, tissue-friendly material having a closed first end and defining an interior cavity for receipt of in-flowing menstrual blood, and having an exterior;
   a plurality of inflow apertures formed in said hollow body and inclined toward said closed first end to permit menstrual blood to flow from exteriorly of said interior cavity into said interior cavity, and to be directed toward said closed first end;
   an at least partially open second end of said interior cavity spaced from said first end and allowing said interior cavity to be accessible from exteriorly of said body; and
   a plurality of inflow grooves axially extending from adjacent said second end of said cavity along said body exterior toward said closed first end of said body.

6. A tampon as recited in claim 5 wherein said grooves terminate at said inflow apertures.

7. A tampon as recited in claim 5 further comprising a plurality of balls of highly absorbent material disposed within said interior cavity.

8. A tampon as recited in claim 5 wherein said body has a substantially elliptical configuration in cross-section.

9. A tampon comprising:
   a hollow body of flexible, human tissue-friendly material, having a lower portion;
   said lower portion of said tampon body being closed and semi-circular in shape;
   said hollow body and closed lower portion defining an interior cavity for the receipt and storage of menstrual blood;
   a plurality of inflow apertures formed in said body, said apertures providing for the flow of menstrual blood therethrough to said interior cavity; and
   said interior cavity being accessible from exteriorly of said body so that said cavity may be filled with absorbent material, and the absorbent material may be removed therefrom, and further comprising removable highly absorbent material disposed within said interior cavity, said highly absorbent material in the form of balls.

10. A tampon as recited in claim 9 wherein said body has a substantially elliptical configuration in cross-section.

11. A tampon comprising:
    a hollow body of flexible, human tissue-friendly material, having a lower portion;
    said lower portion of said tampon body being closed and semi-circular in shape;
    said hollow body and closed lower portion defining an interior cavity for the receipt and storage of menstrual blood;
    a plurality of inflow apertures formed in said body and inclined toward said closed lower portion, said apertures providing for the flow of menstrual blood therethrough to said interior cavity;
    said interior cavity being accessible from the exterior of said body so that said cavity may be filled with absorbent material, and the absorbent material may be removed therefrom; and
    a plurality of balls of highly absorbent material disposed within said interior cavity.

12. A tampon as recited in claim 11 wherein said body has a substantially elliptical configuration in cross-section.

13. A tampon comprising:
    a substantially cylindrical hollow body of flexible, tissue-friendly material having a closed first end and defining an interior cavity for receipt of inflowing menstrual blood;
    a plurality of inflow apertures formed in said hollow body and inclined toward said closed first end to permit menstrual blood to flow from exteriorly of said interior cavity into said interior cavity, and to be directed toward said closed first end;
    an at least partially open second end of said interior cavity spaced from said first end and allowing said interior cavity to be accessible from exteriorly of said body; and
    a plurality of balls of highly absorbent material disposed within said interior cavity.

14. A tampon as recited in claim 13 wherein said body has a substantially elliptical configuration in cross-section.

\* \* \* \* \*